United States Patent
Akutsu

(10) Patent No.: US 8,920,167 B2
(45) Date of Patent: Dec. 30, 2014

(54) SURGICAL GUIDE PREPARATION TOOL AND METHOD FOR PREPARING SURGICAL GUIDE

(75) Inventor: Isao Akutsu, Tokyo (JP)

(73) Assignee: Implantdent Co., Ltd. (JP)

( * ) Notice: Subject to any disclaimer, the term of this patent is extended or adjusted under 35 U.S.C. 154(b) by 0 days.

(21) Appl. No.: 13/819,749

(22) PCT Filed: Sep. 21, 2010

(86) PCT No.: PCT/JP2010/066284
§ 371 (c)(1),
(2), (4) Date: Feb. 28, 2013

(87) PCT Pub. No.: WO2012/039017
PCT Pub. Date: Mar. 29, 2012

(65) Prior Publication Data
US 2013/0171587 A1   Jul. 4, 2013

(51) Int. Cl.
*A61C 19/04* (2006.01)
*A61C 8/00* (2006.01)
*A61C 1/08* (2006.01)
*A61B 6/03* (2006.01)
*A61B 6/14* (2006.01)

(52) U.S. Cl.
CPC ......... *A61C 8/0089* (2013.01); *A61C 2201/005* (2013.01); *A61C 1/084* (2013.01); *A61B 6/032* (2013.01); *A61B 6/145* (2013.01)
USPC ......................................................... 433/72

(58) Field of Classification Search
CPC ........ A61B 6/032; A61B 6/145; A61C 1/084; A61C 2201/005; A61C 8/0089
USPC ...................................................... 433/72–76
See application file for complete search history.

(56) References Cited

U.S. PATENT DOCUMENTS

| 2,448,437 | A | * | 8/1948 | Kaplan | 433/76 |
| 3,436,826 | A | * | 4/1969 | Edelman | 433/75 |
| 5,015,183 | A | * | 5/1991 | Fenick | 433/76 |
| 5,133,660 | A | * | 7/1992 | Fenick | 433/76 |
| 5,320,529 | A | * | 6/1994 | Pompa | 433/76 |
| 5,556,278 | A | * | 9/1996 | Meitner | 433/75 |

(Continued)

FOREIGN PATENT DOCUMENTS

| EP | 1043960 | 10/2000 |
| EP | 1043960 B1 * | 9/2003 |

(Continued)

*Primary Examiner* — Cris L Rodriguez
*Assistant Examiner* — Mirayda A Aponte
(74) *Attorney, Agent, or Firm* — Adams & Wilks

(57) ABSTRACT

The present invention provides an inexpensive surgical guide preparation tool by which an insertion hole for implant can be correctly and easily formed at a predetermined position. The surgical guide preparation tool has a pair of marker members opposing to each other and a gauge body which has a support member for connecting the marker members, and the gauge body is attached to a surgical guide body. The surface of each marker member is provided with grid-like lines which are recognizable by a CT scanned image and disposed longitudinally and laterally at substantially regular intervals; predetermined marks are chosen from intersections of the grid-like lines, and a guide ring is attached to the surgical guide body so that a direction connecting the chosen marks is used as an axial direction of the guide ring. The axial direction of the guide ring is used as an insertion direction for implant.

10 Claims, 9 Drawing Sheets

(56) References Cited

U.S. PATENT DOCUMENTS

| | | | |
|---|---|---|---|
| 5,636,986 A * | 6/1997 | Pezeshkian | 433/76 |
| 5,641,287 A * | 6/1997 | Gittleman | 433/75 |
| 5,688,283 A * | 11/1997 | Knapp | 606/96 |
| 5,718,579 A * | 2/1998 | Kennedy | 433/75 |
| 5,725,376 A * | 3/1998 | Poirier | 433/172 |
| 5,769,636 A * | 6/1998 | Di Sario | 433/213 |
| 5,915,962 A * | 6/1999 | Rosenlicht | 433/76 |
| 5,967,777 A * | 10/1999 | Klein et al. | 433/75 |
| 6,814,575 B2 * | 11/2004 | Poirier | 433/75 |
| 6,966,772 B2 * | 11/2005 | Malin et al. | 433/75 |
| 6,971,877 B2 * | 12/2005 | Harter | 433/75 |
| 6,997,707 B2 * | 2/2006 | Germanier | 433/75 |
| 7,014,461 B2 * | 3/2006 | Weinstein | 433/76 |
| 7,044,735 B2 * | 5/2006 | Malin | 433/75 |
| 7,097,451 B2 * | 8/2006 | Tang | 433/76 |
| 7,331,786 B2 * | 2/2008 | Poirier | 433/75 |
| 7,429,175 B2 * | 9/2008 | Gittelson | 433/75 |
| 7,682,151 B2 * | 3/2010 | Jofre Araya | 433/75 |
| 7,731,497 B2 * | 6/2010 | De Moyer | 433/72 |
| 7,835,811 B2 * | 11/2010 | Schmitt | 700/98 |
| 7,845,943 B2 * | 12/2010 | Meitner | 433/75 |
| 7,866,980 B2 * | 1/2011 | Poirier | 433/75 |
| 7,950,924 B2 * | 5/2011 | Brajnovic | 433/75 |
| 8,038,440 B2 * | 10/2011 | Swaelens et al. | 433/76 |
| 8,105,081 B2 * | 1/2012 | Bavar | 433/75 |
| 8,142,189 B2 * | 3/2012 | Brajnovic | 433/75 |
| 8,157,563 B2 * | 4/2012 | Brajnovic | 433/75 |
| 8,215,957 B2 * | 7/2012 | Shelton | 433/75 |
| 8,231,386 B2 * | 7/2012 | Hertz | 433/173 |
| 8,419,426 B2 * | 4/2013 | Paris et al. | 433/75 |
| 8,435,033 B2 * | 5/2013 | Gross et al. | 433/75 |
| 8,439,675 B2 * | 5/2013 | De Moyer | 433/75 |
| 8,579,628 B2 * | 11/2013 | Drews et al. | 433/75 |
| 2004/0219477 A1 * | 11/2004 | Harter | 433/75 |
| 2005/0170311 A1 * | 8/2005 | Tardieu et al. | 433/76 |
| 2005/0287492 A1 * | 12/2005 | Lazzarato | 433/72 |
| 2006/0257817 A1 * | 11/2006 | Shelton | 433/75 |
| 2007/0077532 A1 * | 4/2007 | Harter | 433/75 |
| 2007/0224574 A1 * | 9/2007 | Poirier | 433/75 |
| 2008/0057467 A1 * | 3/2008 | Gittelson | 433/72 |
| 2009/0017418 A1 * | 1/2009 | Gittelson | 433/75 |
| 2009/0176187 A1 * | 7/2009 | Esposti et al. | 433/72 |
| 2009/0202959 A1 * | 8/2009 | Ajlouni et al. | 433/76 |
| 2009/0298008 A1 * | 12/2009 | Groscurth et al. | 433/74 |
| 2010/0035201 A1 * | 2/2010 | Beck et al. | 433/76 |
| 2010/0136500 A1 * | 6/2010 | Suter et al. | 433/75 |
| 2010/0173259 A1 * | 7/2010 | Vogel et al. | 433/72 |
| 2010/0173260 A1 * | 7/2010 | Sogo et al. | 433/75 |
| 2010/0291504 A1 * | 11/2010 | Paris et al. | 433/72 |
| 2010/0297574 A1 * | 11/2010 | Llop et al. | 433/75 |
| 2011/0004276 A1 * | 1/2011 | Blair et al. | 607/60 |
| 2011/0045431 A1 * | 2/2011 | Groscurth et al. | 433/74 |
| 2011/0091836 A1 * | 4/2011 | Fujii | 433/75 |
| 2011/0143307 A1 * | 6/2011 | Takebayashi | 433/74 |
| 2011/0256500 A1 * | 10/2011 | Crudo | 433/75 |
| 2011/0275032 A1 * | 11/2011 | Tardieu et al. | 433/174 |
| 2011/0306009 A1 * | 12/2011 | Suttin et al. | 433/75 |
| 2011/0311941 A1 * | 12/2011 | Yi et al. | 433/75 |
| 2012/0028213 A1 * | 2/2012 | Meitner | 433/74 |
| 2012/0164593 A1 * | 6/2012 | Bavar | 433/29 |
| 2012/0196250 A1 * | 8/2012 | Grant et al. | 433/174 |
| 2012/0316486 A1 * | 12/2012 | Cheung et al. | 602/48 |
| 2013/0011813 A1 * | 1/2013 | Alvarez Garcia et al. | 433/173 |
| 2013/0023888 A1 * | 1/2013 | Choi et al. | 606/96 |
| 2013/0071811 A1 * | 3/2013 | Groscurth et al. | 433/75 |
| 2013/0280673 A1 * | 10/2013 | Maksim | 433/75 |

FOREIGN PATENT DOCUMENTS

| | | |
|---|---|---|
| EP | 1364625 A1 * | 11/2003 |
| JP | 2006141561 A * | 6/2006 |
| JP | 2010142537 | 7/2010 |
| WO | WO 9743981 A1 * | 11/1997 |
| WO | WO 03073954 A1 * | 9/2003 |
| WO | 2008149822 | 12/2008 |
| WO | WO 2008149822 A1 * | 12/2008 |
| WO | 2009119620 | 10/2009 |
| WO | WO 2009119620 A1 * | 10/2009 |

* cited by examiner

SURGICAL GUIDE PREPARATION TOOL AND METHOD FOR PREPARING SURGICAL GUIDE

FIELD OF THE INVENTION

The present invention relates to a surgical guide preparation tool for placing a dentistry implant at a predetermined position, and a method for preparing a surgical guide.

BACKGROUND INFORMATION

In recent years, dentistry treatments to form a denture by embedding an implant (artificial tooth root) in a tooth deficient portion have been performed. In such treatments, insertion holes for implant are drilled at tooth deficient portions by use of a drill attached to a drilling apparatus such as a handpiece, and at this time, a surgical guide is usually employed to drill a hole in order to guide the drill so that the hole for implant would be formed at a predetermined position and in a predetermined direction.

Into this surgical guide, a metallic guide ring (guide tube) is fitted to guide the drill to the surgical guide supported by jawbone, etc.

When the guide ring is employed to guide the drill for drilling a hole, it is required that adequate bone quantity is confirmed at the portion where the hole for implant is formed and no nerves or blood vessels are present at this portion.

In order to satisfy such requirements, in general, a CT scanning is conducted by use of an X-ray CT apparatus (Computed Tomography) in such a state that a surgical guide (a stent for diagnosis) is attached to the teeth of the patient, and the examination results by the CT scanned image are used to determine the insertion direction of the implant.

Various methods have been proposed as a method for determining the insertion direction of the implant.

For example, European Patent No. 1043960 describes a method for processing a hole for implant by a numerically controlled boring machine which moves in relation with an X-ray CT apparatus.

In this method, since the numerically controlled boring machine is additionally employed, the entire machine becomes large, the operation requires skillfulness and costs become high.

Further, as described in JP-A-2006-141561, a method has been proposed in that the CT scanned image of a jaw bone area of a tooth deficient portion is printed, the tooth deficient portion is cut out from the print, the cutout part is adhered to a teeth impression model, and then the adhered cutout part is given a mark showing the insertion position and direction of implant, and a hole for implant is drilled along this mark.

However, in this method, many operations are required as described above and the hole for implant is processed while visually observing the mark, whereby there is a concern that the hole for implant may not be processed correctly.

PRIOR ART DOCUMENTS

Patent Documents

Patent document 1: European Patent No. 1043960
Patent document 2: JP-A-2006-141561

SUMMARY OF THE INVENTION

Problems that the Invention is to Solve

The present invention is to solve such problems and provide a surgical guide preparation tool and a method for preparing the surgical guide, whereby a hole for implant can be formed at a predetermined position correctly and easily.

Means of Solving the Problems

The present invention provides a gauge body having a pair of marker members each of which has plural marks which are recognizable by a CT scanned image and disposed longitudinally and laterally at substantially regular intervals. Using a surgical guide preparation tool comprising the gauge body attached to a surgical guide body, predetermined marks are chosen from the plural marks on the marker members, and the direction connecting the chosen marks is used as the direction of the hole for implant. To the marker members, a support member for supporting the marker member is provided.

Further, in the present invention, it is possible to detachably install an X-ray impermeable artificial tooth which can be recognized by a CT scanned image at the internal side of the gauge body, and confirm the positional relation between the direction of the hole for implant and the artificial tooth.

Furthermore, the method for preparing a surgical guide of the present invention comprises a step of preparing the above gauge body; a step of installing the gauge body at a position of the surgical guide body that corresponds to a deficient tooth, capturing into a computer a CT scanned image obtained in such a state that the surgical guide body is positioned on the teeth, and reading the positions of marks of both marker members corresponding to the insertion direction of the implant by analysis with computer operation; a step of inserting a positioner into the internal side of the guide ring, inserting the guide ring into the internal side of the gauge body, and inserting a pin in such a direction connecting the axis of the positioner and the position of the marks of respective marker members from which the insertion direction of the implant has been read; a step of fixing the guide ring to the surgical guide body at such position where the pin is inserted, and then removing the pin, positioner and gauge body.

In addition to the above steps, the method for preparing a surgical guide of the present invention further comprises a step of detachably installing the X-ray impermeable artificial tooth which can be recognized by a CT scanned image at the internal side of the gauge body, and removing the artificial tooth when the guide ring is inserted into the internal side of the gauge body; and a step of forming a slit on the guide ring so that a blade portion of a drill for boring a jaw bone can be inserted from the side face of the guide ring, and forming an opening portion of which the width is substantially the same as the slit or expands outwardly and more widely than the slit at a position of the surgical guide body corresponding to the slit.

The surgical guide is a support having a guide ring, and this is classified into a type supported by jaw bone, a type supported by gum, and a type supported by teeth. All of the surgical guides of these types are generally made of a plastic material. If the surgical guide is made of a transparent material, the operation site can be easily seen.

The guide ring to be installed in the surgical guide is made of a metal such as titanium or aluminum or a hard plastic material, with an inner diameter of about 4 mm to 9 mm and an outer diameter of about 5 mm to 10 mm so that it will suit the diameter of a guide member of a drill. However, the size is not limited to these ranges.

At the side face of the guide ring, a slit is formed so that the front end portion of an implant medical instrument such as a blade portion of a drill, an implant and an adaptor for inserting the implant can be inserted from its sidewise direction. At a position of the surgical guide body corresponding to the slit, the surgical guide body is provided with an opening portion of which the width is substantially the same as the slit or expands outwardly and more widely than the slit.

Since the diameter of the blade portion of the drill is generally about 2 mm to 5 mm to suit to the diameter of the implant, the width of the slit is about 4 mm to 6 mm which is a little larger than the maximum diameter of the implant to be used. However, the width of the slit is not limited to this range.

If the upper part of the guide ring is outwardly expanded in a tapered shape, the drill can be easily guided.

The gauge body is installed in the surgical guide body. The gauge body has a pair of marker members opposing to each other, and the marker members may have a surface configuration of quadrilateral, rectangular, circular, elliptical, trapezoidal, etc. As the size of the gauge body, when it is used for one tooth deficient portion, the lengthwise and lateral widths are about 10 to 20 mm, the height is about 10 to 30 mm, and the thickness is about 1 to 2 mm. However, the size is not limited to these ranges. When it is used for adjoining plural teeth deficient portion, the width is of course adjusted suitably to the number of teeth.

The surfaces of the pair of marker members of the gauge body are provided with marks which are recognizable by a CT scanned image and disposed longitudinally and laterally at substantially regular intervals. The marks may be provided on the side faces of the marker members.

When the pair of marker members is made of an X-ray permeable member, for example, an X-ray permeable plastic material, grid-like lines or grooves are formed by coating the marker member surfaces with an X-ray impermeable material (e.g. barium sulfate, bismuth oxide, bismuth subcarbonate, etc.) and intersections of these lines or grooves are used as marks, or an X-ray impermeable material is embedded in grid-like or dot-like form on the marker member surface and the intersections of the grid or the dots are used as marks. In this instance, when a pigment, a coating, etc. is blended to the X-ray impermeable material for coloration, the marks can be further easily seen.

The intersection portions may be provided with small holes, and a part of the small holes (a hole located at the center of the marker member, or a hole located at the end thereof) may be formed larger than others and used as a standard hole. The size of the small holes is about 1 mm in diameter, but may be of other diameter.

On the other hand, when the pair of marker members is made of an X-ray impermeable material, for example, a metallic material or a plastic material having an X-ray impermeable material blended, small holes or standard holes are disposed at the positions as the intersections of grid-like lines, and such small holes are used as marks. In this instance, it is advisable that grid-like lines are given on the surfaces of the pair of marker members so that the grid-like lines can be visually observed.

The position of mark is not limited to just on the grid-like lines, and it may be located at the intersections of appropriately shaped-lines such as a spider web-like or ripple-like shape so far as the position can be recognized by a CT scanned image. Further, a metallic mesh material may be used as the marker member, and in this instance, the holes of the mesh are used as the position of mark.

The marks are formed at intervals of about 1 to 2 mm, but may have other intervals. Further, the marks are formed to have a depth of about 0.5 to 1 mm, but may have other depth.

Since the internal side of the gauge body is space, the artificial tooth corresponding to the tooth deficient portion can be inserted into this space. The artificial tooth is temporarily fixed to the lower marker member, a support member, etc. of the gauge body, with a polymerizable resin, etc. Further, the surface of the artificial tooth is recognizable by the CT scanned image by coating the surface with an X-ray impermeable material or producing the artificial tooth integrally with an X-ray impermeable material. By installing the artificial tooth within the internal side of the gauge body, it is possible to observe the occluded condition of teeth in the insertion direction of implant and install the artificial tooth at the predetermined position and in the predetermined direction. The artificial tooth may sometimes be omitted.

A surgical guide preparation tool comprising a surgical guide body and a gauge body attached thereto or a surgical guide preparation tool comprising a surgical guide body and a gauge body with the artificial tooth, attached thereto, is installed in a portion corresponding to the patient's deficient tooth, and subjected to CT scanning with an X-ray CT scanning machine to obtain a CT scanned image. This CT scanned image is captured into a computer, and analyzed by use of a CT scanned image analyzing software (for example, a software such as One Volume Viewer: J. MORITA MFG. CORP.), and while confirming the marks of respective marker members of the gauge body and the position of the artificial tooth, the position of mark corresponding to the insertion position and direction of implant is determined. The above CT scanned image may be at first stored in a recording medium such as CD or DVD and then captured into a computer; or the X-ray CT scanning machine may be connected to a computer, and the CT scanned image may be directly captured into the computer.

After the CT scanning, the surgical guide preparation tool is removed from the patient, a pin made of a metal such as stainless steel or a tough plastic is inserted into a small hole as the mark of each marker member determined as above. If no small hole is formed, a small hole may be perforated by a pointed pin. The direction of this pin is used as the predetermined insertion direction of implant.

Here, the pin is temporarily pulled out, a positioner is inserted into the guide ring, this guide ring is inserted into the internal space of the gauge body, and the pin is again inserted into the small hole as the mark and the hole at the center of the positioner. Under this condition, a fixing material such as a polymerizable resin is filled around the guide ring to fix the guide ring to the surgical guide body.

After the fixing material is cured, the pin is removed, and then the gauge body and the positioner are removed to complete the surgical guide. The positioner is usually made of a plastic material (including a foamed material), but may be made of other materials.

Effects of the Invention

In the present invention, as described above, it is possible to correctly match the position and direction of the guide ring attached to the surgical guide with the insertion position and direction of the implant, and therefore the precision of implant treatment can be increased and costs can be reduced. Further, by using the preparation tool and preparation method of the present invention, it becomes possible to improve the safety in implant operation and shorten the operation time, whereby the mental burden of the patients, operators and medical staff can be reduced, treatment results can be improved, and the economic burden on patients and clinics can be reduced.

BRIEF DESCRIPTION OF THE DRAWINGS

FIGS. 11A-11C are collectively an exploded perspective view of an assembled gauge body showing another example, wherein FIG. 11A shows an upper member, FIG. 11B shows a lower member and FIG. 11C shows a base plate.

FIGS. 12A-12D are collectively an exploded perspective view of an assembled gauge body showing a further example, wherein FIG. 12A shows an upper frame member, FIG. 12B shows an upper marker member, FIG. 12C shows a lower frame member and FIG. 12D shows a lower marker member.

FIGS. 13A-13D are collectively an exploded perspective view of a gauge body showing another example, wherein FIG. 13A shows an upper frame, FIG. 13B shows an upper marker member, FIG. 13C shows a lower frame and FIG. 13D shows a lower marker member.

DETAILED DESCRIPTION OF THE PREFERRED EMBODIMENTS

Hereinafter, the surgical guide preparation tool and the method for preparing the surgical guide will be explained.

Figure 1:
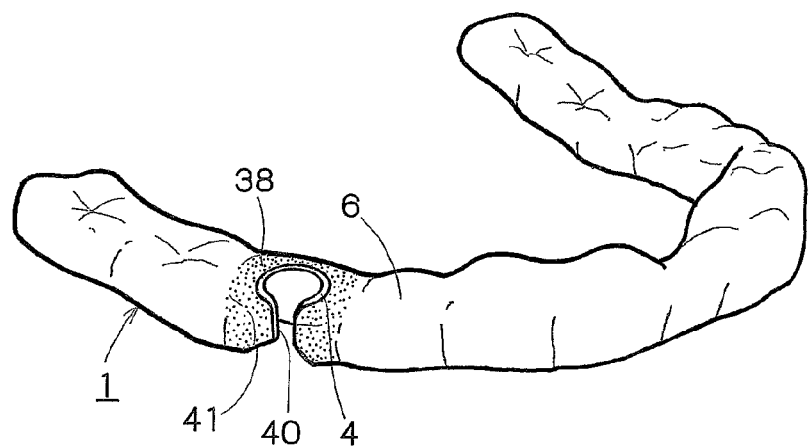
FIG. 1 is a perspective view of a surgical guide showing an example of the present invention.
Figure 2:
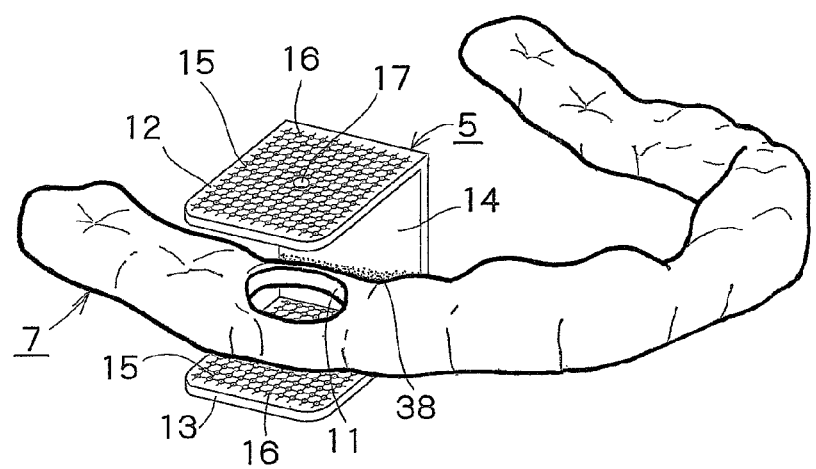
FIG. 2 is a perspective view of a surgical guide preparation tool.
Figure 14:
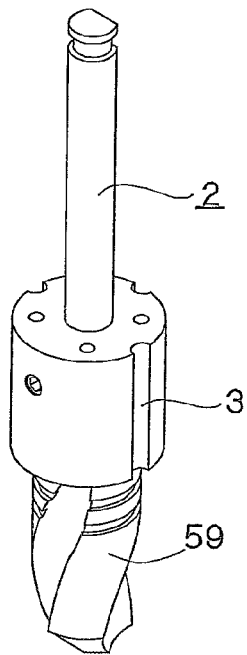
FIG. 14 is a perspective view of a drill.

A surgical guide 1 shown in FIG. 1 has a guide ring 4 which guides a guide member 3 of a drill 2 shown in FIG. 14. This guide ring 4 is attached to a surgical guide body 6 so that the installed position and direction of the guide ring would match the insertion position and direction of an implant. The attachment is carried out by a surgical guide preparation tool 7 comprising surgical guide body 6 (shown in FIG. 4.) and a gauge body 5 (shown in FIG. 2) attached thereto, as shown below.

Figure 3:
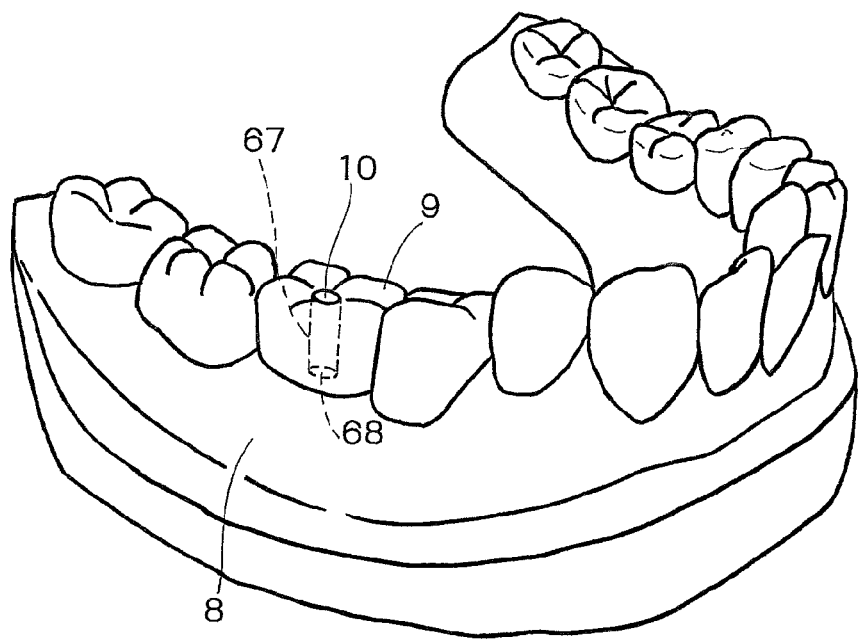
FIG. 3 is a perspective view of a lower jaw teeth impression model.

As shown in FIG. 3, firstly, a patient's lower jaw teeth impression model 8 and an artificial tooth 9 which corresponds to a deficient tooth are prepared; and a pin 10 is put into a hole 68 of the lower jaw teeth impression model 8 which is presumed to be bored at an appropriate position and in an appropriate direction, through a center hole 67 of the artificial tooth 9, and then the artificial tooth 9 is temporarily fixed to the lower jaw teeth impression model 8. The surface of the artificial tooth 9 is coated with an X-ray impermeable material.

Figure 4:
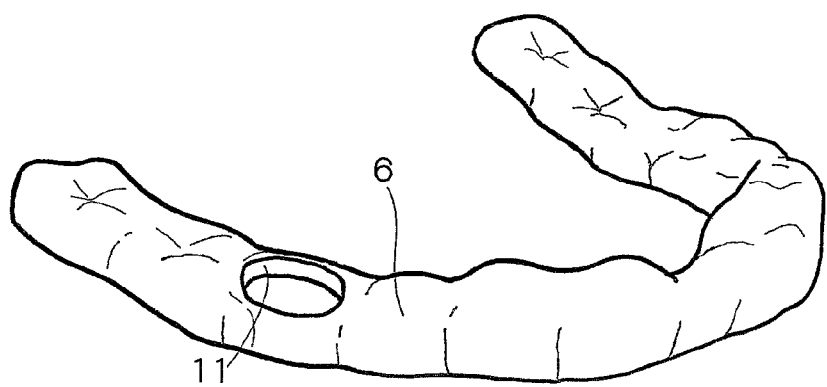
FIG. 4 is a perspective view of a surgical guide body.

Then, the surgical guide body 6 is prepared by using the lower jaw teeth impression model 8. At a portion of the surgical guide body 6 which corresponds to the deficient tooth, a hole 11 is formed so that a part of the upper portion of the artificial tooth 9 would be exposed as shown in FIG. 4.

Figure 5:
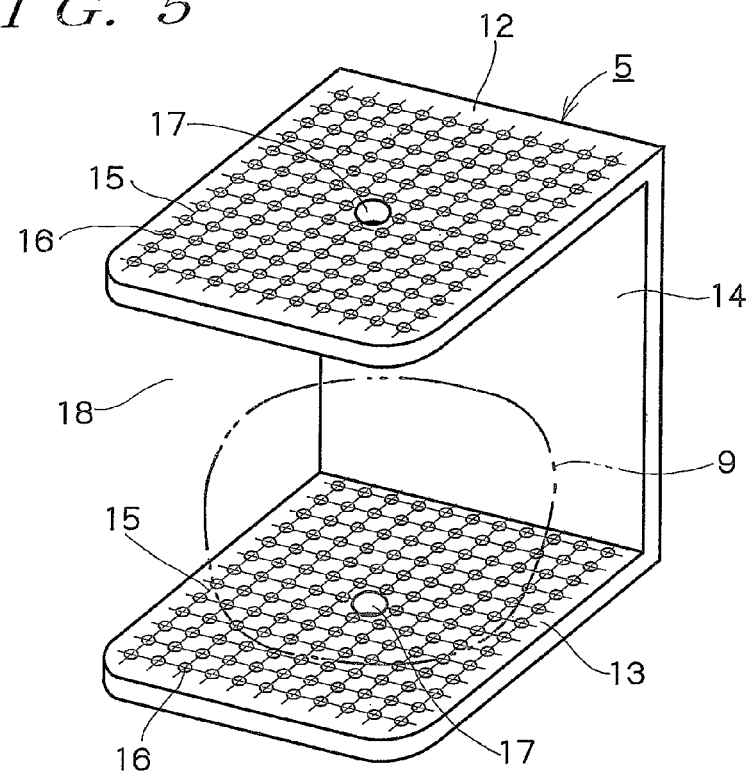
FIG. 5 is a perspective view of a gauge body.

As shown in FIG. 5, the gauge body 5 comprises an upper marker member 12, a lower marker member 13 and a support member 14 which connects the pair of marker members. As illustrated, the marker members 12,13 have a plate-shaped configuration. The gauge body 5 is generally prepared integrally with a plastic material having X-ray impermeability. The marker members 12,13 are spaced apart from one another to form therebetween a hollow internal space 18 configured to receive therein the artificial tooth 9.

The surfaces of the marker members 12, 13 are given grid-like lines 15, and at the intersections of the lines, small holes 16 are bored. A hole at the center portion of the marker member is formed to have a larger diameter than that of small holes 16 and is used as a standard hole 17.

Figure 6:
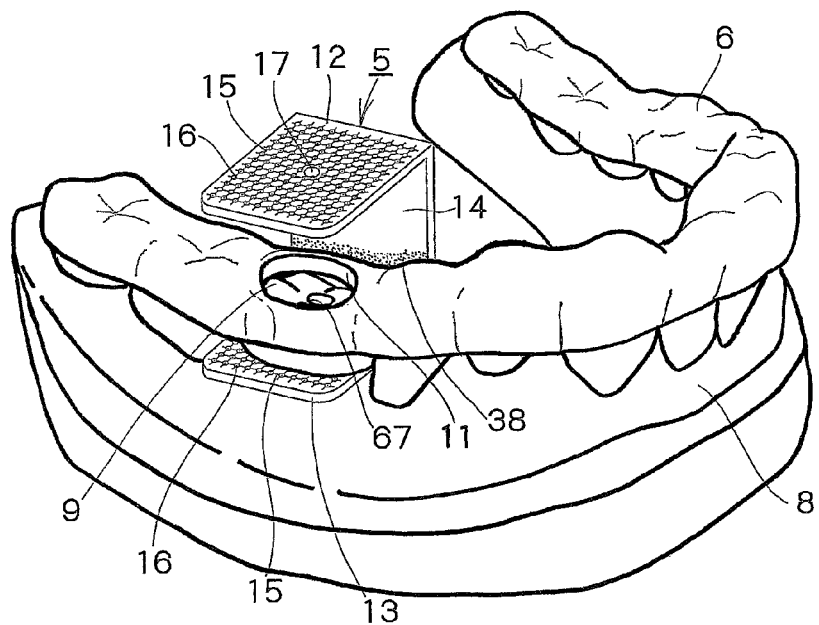
FIG. 6 is a perspective view showing a state where a surgical guide preparation tool is attached to a lower jaw teeth impression model.

Here, as shown in FIG. 6, the artificial tooth 9 and pin 10 are removed from the lower jaw teeth impression model 8, and the artificial tooth 9 is inserted into an the hollow internal space 18 of the gauge body 5 and placed on the lower marker member 13. And, the position of the gauge body 5 is determined by putting a pin 35 through the standard hole 17 of the gauge body 5, a hole 67 at the center of the artificial tooth and a hole 68 of the lower jaw teeth impression model 8. When the support member 14 of the gauge body 5 abuts on the side face of the surgical guide body 6, a part of the side face portion of the surgical guide body 6 is removed.

In this instance, in order to allow the lower marker member 13 of the gauge body 5 to be inserted into the lower side of the surgical guide body 6, the lower portion of the artificial tooth 9 is preliminarily removed in such a thickness corresponding to the thickness of the lower marker member 13 to adjust the installation height of the artificial tooth 9, and then the artificial tooth 9 is temporarily fixed at a predetermined position by use of a polymerizable resin, an adhesive, etc. Thereafter, the surgical guide body 6 and the gauge body 5 are fixed with fixing material 38 such as a polymerizable resin, and then the pin 35 is pulled out to complete the surgical guide preparation tool 7.

The thus prepared surgical guide preparation tool 7 is attached to the patient's teeth, and a CT scanned image 20 is obtained by CT scanning with an X-ray CT scanning machine 19.

Figure 15:
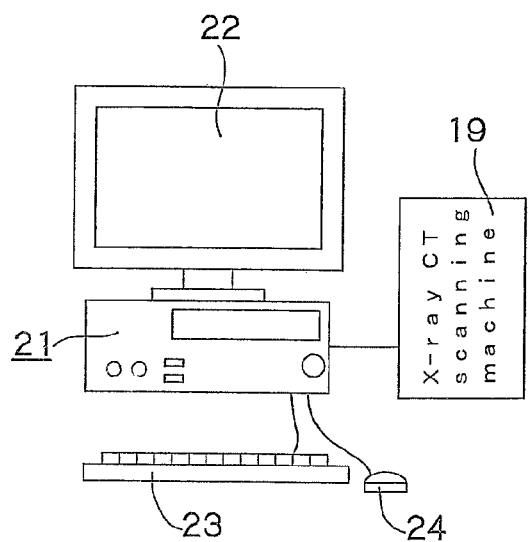
FIG. 15 is a schematic view of a computer system for analysis of a CT scanned image.

As shown in FIG. 15, the CT scanned image 20 is captured into a computer 21 (provided with a monitor 22, a key board 23 and a mouse 24), the image is analyzed with use of a CT scanned image analyzing software installed in the computer 21, and the positions of marks of the pair of marker members 12, 13 which correspond to the insertion direction of implant are recognized.

Figure 7:
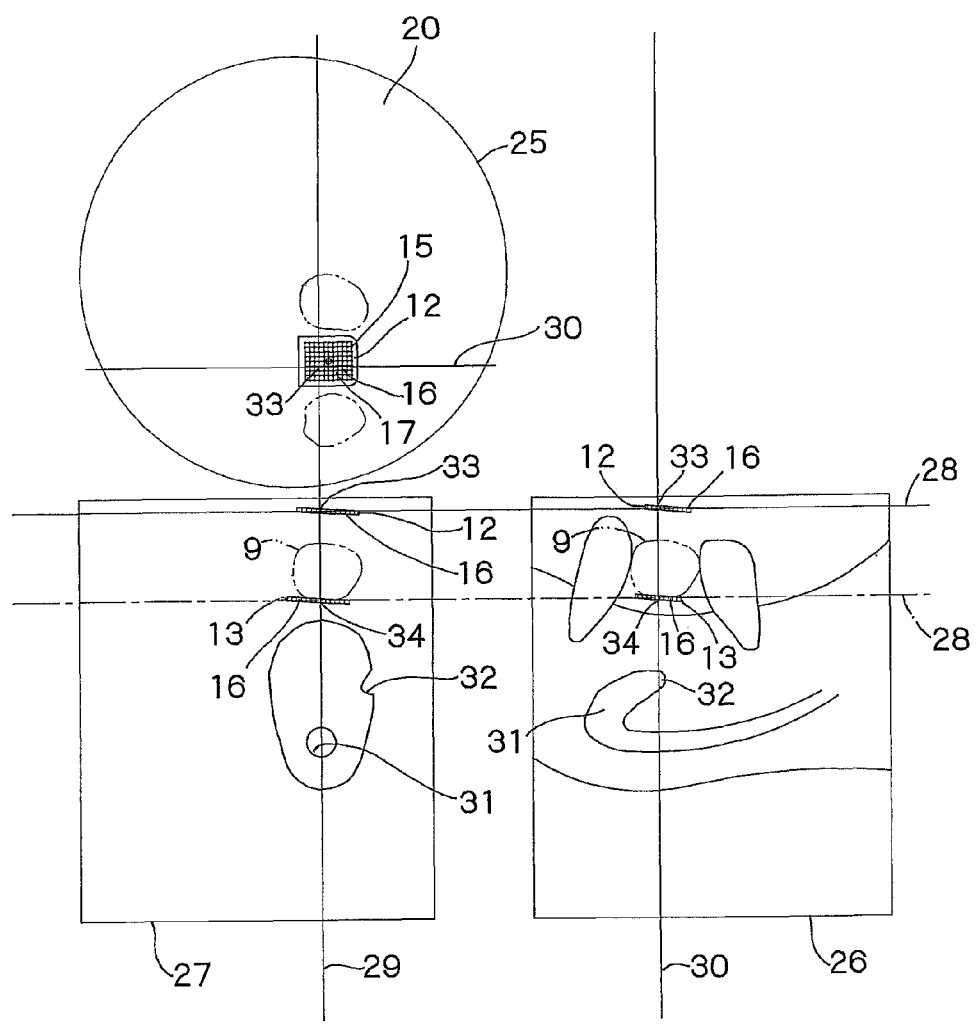
FIG. 7 is a schematic view showing a CT scanned image taken when a surgical guide preparation tool is attached to the patient's teeth.

Namely, as shown in FIG. 7, an axial section 25, a panorama section 26 and an orthoradial section 27 are displayed by operation of the computer 21, and while confirming the positions of respective marker members of the gauge body, a panorama cutting line 29 and an orthoradial cutting line 30 are moved on these sections in such a direction that the implant is to be inserted. After confirming that sufficient jaw bone is present in the directions of the panorama cutting line 29 and the orthoradial cutting line 30 on the panorama section 26 and the orthoradial section 27 and further confirming that nerves and blood vessels 31, 32 are not present at these sites, these directions are determined to be an insertion direction of implant.

In the determined direction, by moving an axial cutting line 28, marks 33, 34 of respective marker members positioned at the intersections of the above cutting lines are read as marks corresponding to the insertion direction of implant. At this instance, the positions of the marks 33, 34 can be determined by reading the distance of the small holes or scale on the CT scanned image from the standard hole 17.

Figure 8:
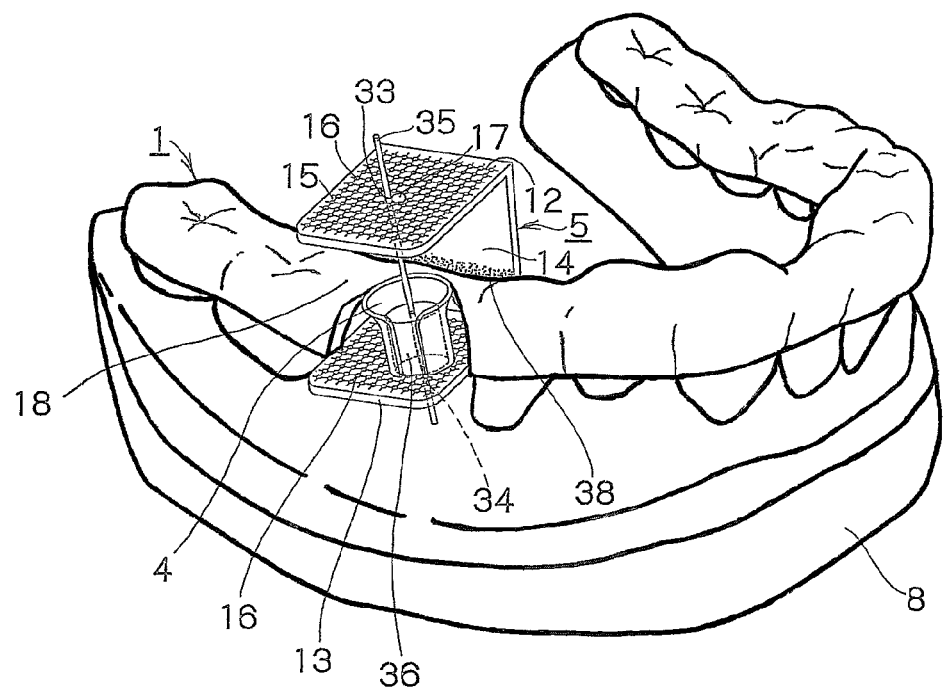
FIG. 8 is a perspective view showing a state where a guide ring is inserted into the internal space of a gauge body.
Figure 9:
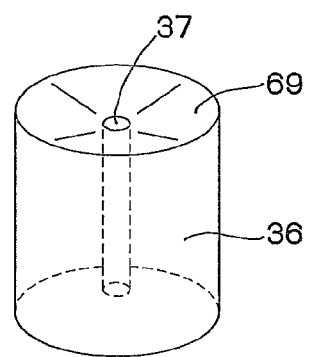
FIG. 9 is an enlarged perspective view of a positioner.
Figure 10:
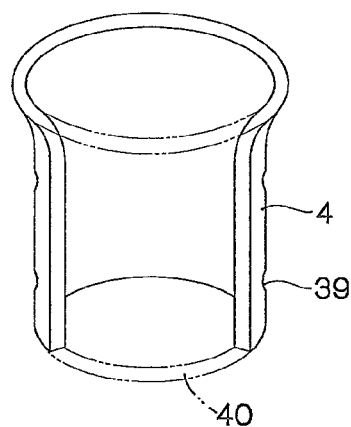
FIG. 10 is an enlarged perspective view of a guide ring.

Next, as shown in FIG. 8, a part of the surgical guide preparation tool 7 is removed and the artificial tooth 9 is taken out, and then the pin 35 is inserted into two holes formed at the marks 33, 34 of respective marker members which have been read. Before the pin is inserted, a positioner 36 shown in FIG. 9 is inserted into the guide ring 4 shown in FIG. 10, and this guide ring 4 is inserted into the internal space 18 of the gauge body 5. And, the pin 35 is put into a hole 37 at the center of the positioner 36. At both or either one of edge faces of the positioner 36, a funnel-shaped convex face 69 is formed, and the front end part of the pin 35 can be guided with the convex face 69 and can be easily inserted into the hole 37 at the center of the positioner 36.

Under such condition, a fixing material 38 such as a polymerizable resin is filled around the guide ring 4, and the guide ring 4 is connected to the surgical guide body 6 to integrate them. Thereafter, the pin 35, positioner 36 and gauge body 5 are removed to complete the surgical guide 1 as shown in FIG. 1. After removing the gauge body 5, etc., if necessary, a fixing material such as a polymerizable resin may be supplied to a connecting portion of the guide ring 4 and the surgical guide body 6.

Around the guide ring 4, a convex 39 or concave is formed, by which rotating motion of the guide ring 4 can be prevented.

The surgical guide 1 is provided with an opening portion 41 expanding outwardly so that it would have a width larger than the width of a slit 40 of the guide ring as shown in FIG. 1. The width of the slit 40 is at such a level of allowing a blade portion 59 for dentistry to pass therethrough as shown in FIG. 14, and the inner diameter of the guide ring is at such a level of allowing the guide member 3 of the drill 2 to be slidably guided.

Figure 11A:
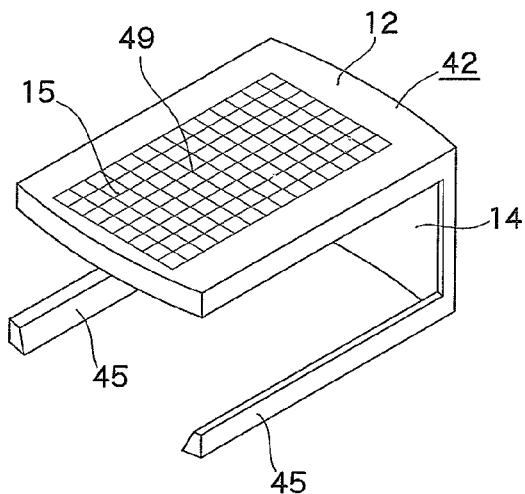
Figure 11B:
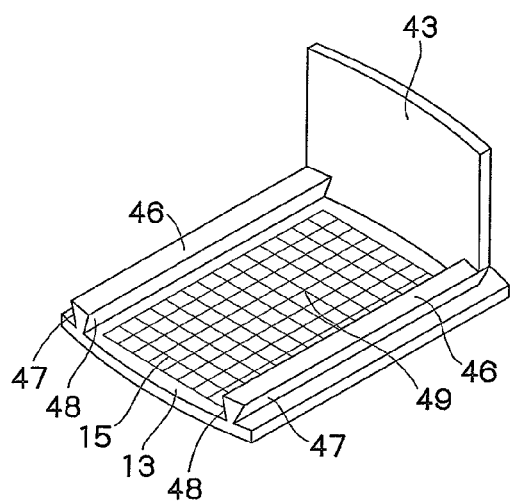
Figure 11C:
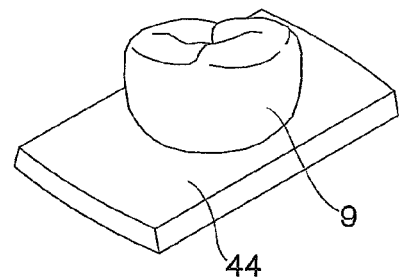
Figure 12A:
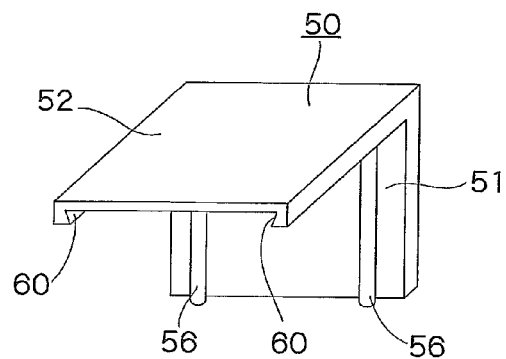
Figure 12B:
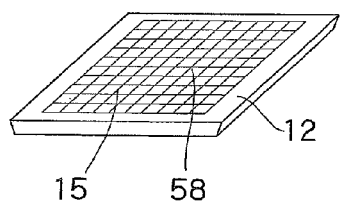
Figure 12C:
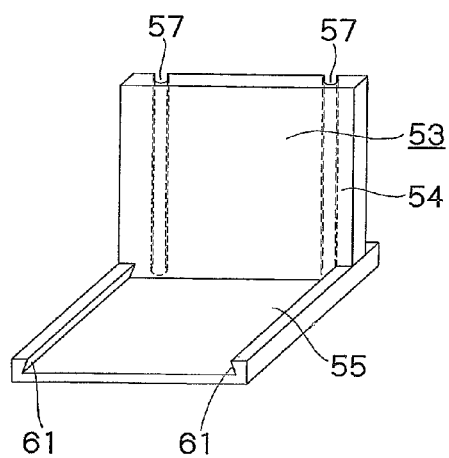
Figure 12D:
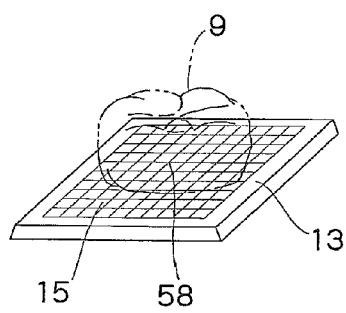
Figure 13A:
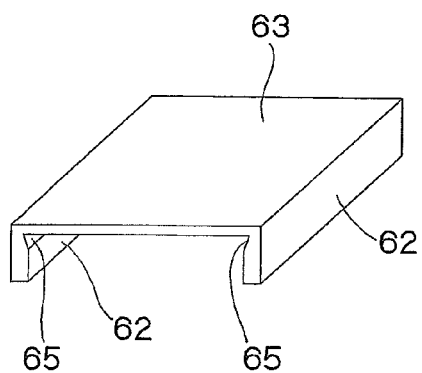
Figure 13B:
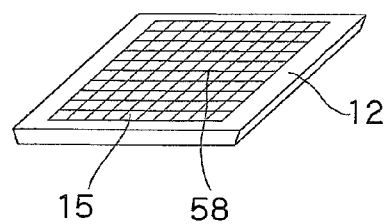
Figure 13C:
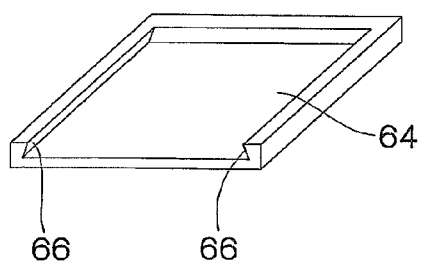
Figure 13D:
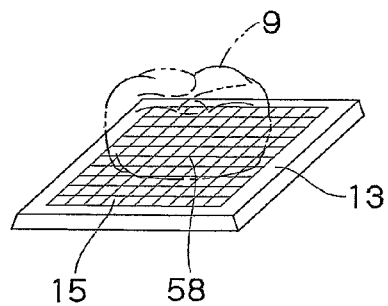

The gauge body 5 shown in FIGS. 11A-11C is of an assembly type, and comprises an upper member 42 (FIG. 11A) having an upper marker member 12 and a support member 14 integrally formed, a lower marker member 13 (FIG. 11B) provided with a support plate 43, and a base plate 44 (FIG. 11C) for supporting the artificial tooth 9. A support frame 45 extends from the lower end portion of the upper member 42, and this support frame 45 engages in a dovetail groove 47 formed by a projection 46 disposed on the lower marker member 13. Further, the base plate 44 engages in a dovetail groove 48 formed by the projection 46 disposed on the lower marker member 13. On the surfaces of the upper marker member 12 and lower marker member 13, marks 49 drawn in grid-like form with an X-ray impermeable material are indicated. In this example, a base plate 44 is disposed. However, in a case where the artificial tooth 9 is directly supported by the lower marker member 13, the base plate 44 is omitted.

The gauge body 5 shown in FIGS. 12A-12D shows another assembly type, and comprises an upper marker member 12 (FIG. 12B); an upper frame member 52 (FIG. 12A) having an upper frame 50 supporting the upper marker member 12, and one support member 51, integrally constituted; a lower marker member 13 (FIG. 12D); a lower frame member 55 (FIG. 12C) having a lower frame 53 supporting the lower marker member 13, and another support member 54, integrally constituted; and the artificial tooth 9. The upper marker member 12 engages in a dovetail groove 60 disposed on the upper frame 50, and the lower marker member 13 engages in a dovetail groove 61 disposed on the lower frame member 55. Another support member 51 for the upper frame member 52 and another support member 54 for the lower frame member 55 are connected by engaging a concave-type projection 56 and a convex-type groove 57 formed on these support members, respectively. In this example, the upper frame member 52 and the lower frame member 55 are made of a transparent material; the positions of marks 58 obtained by analysis of a CT scanned image are indicated on the upper frame 50 and the lower frame 53; and the upper frame member 52 and the lower frame member 55 are used as expendable supplies, and the upper marker member 12 and the lower marker member 13 are reused as master pieces.

The gauge body 5 shown in FIGS. 13A-13D comprises the upper marker member 12 (FIG. 13B); an upper frame 63 (FIG. 13A) which has a support portion 62 and supports the upper marker member 12; a lower marker member 13 (FIG. 13D); a lower frame 64 (FIG. 13C) which supports the lower marker member 13; and the artificial tooth 9. The upper marker member 12 engages in a dovetail groove 65 disposed on the support portion 62 of the upper frame 63, and the lower marker member 13 engages in a dovetail groove 61 disposed on the lower frame 64.

EXPLANATION OF NUMERALS

1 Surgical guide
4 Guide ring
5 Gauge body
6 Surgical guide body
8 Lower jaw teeth impression model
9 Artificial tooth
12 Upper marker member
13 Lower marker member
14 Support member
16 Small hole
17 Standard hole
19 X-ray CT scanning machine
20 CT scanned image
21 Computer
33, 34, 49, 58 Marks
35 Pin
36 Positioner
40 Slit
41 Opening portion

The invention claimed is:

1. A gauge body attachable to a surgical guide body having one or more artificial teeth for use in dentistry implant treatment, the gauge body comprising: a pair of marker members attachable during use of the gauge body to a surgical guide body having one or more artificial teeth, the marker members being opposed to and spaced from each other to form therebetween a predetermined hollow space at a position corresponding to the one or more artificial teeth, wherein the predetermined hollow space is configured to receive therein the one or more artificial teeth, and wherein surfaces of the marker members are provided with plural marks which are recognizable on a recorded image.

2. A gauge body according to claim 1; further comprising a support member for connecting the pair of marker members at a predetermined spaced-apart distance.

3. A gauge body according to claim 2; further comprising a support frame extending from an end portion of the support member in the same direction that one of the marker member extends, the support frame having a guide groove which guides and supports the one marker member.

4. A gauge body according to claim 1; wherein the marks are holes or grid-like lines, which are recognizable on a recorded image.

5. A gauge body according to claim 1; wherein the marker members have a plate-shaped configuration.

6. A gauge body according to claim 5; wherein the marker members, when attached to the surgical guide body, are disposed on opposite outer sides of the surgical guide body.

7. A gauge body according to claim 1; wherein the marker members, when attached to the surgical guide body, are disposed on opposite outer sides of the surgical guide body.

8. A method for preparing a surgical guide using the gauge body as defined in claim 1, the method comprising:
- installing the gauge body at a position corresponding to the one or more artificial teeth of the surgical guide body;
- indicating, with the marks of the gauge body, a position showing an insertion direction of an implant for each artificial tooth determined by analysis of a recorded image obtained under such condition that the surgical guide body is attached to the artificial tooth, to determine the insertion direction of each implant;
- inserting a positioner into an internal side of a guide ring for each artificial tooth which is installed in the surgical guide body;
- inserting a pin in a direction connecting the axis of the positioner and a position on each marker member which corresponds to the insertion direction of the implant; and
- installing the guide ring in the surgical guide body in the insertion direction of the pin.

9. A method for preparing a surgical guide according to claim 8; further comprising:
- installing one or more artificial teeth which are recognizable on a recorded image in the hollow predetermined space of the gauge body; and
- removing each artificial tooth when the corresponding guide ring is inserted into the predetermined hollow space of the gauge body.

10. A method for preparing a surgical guide according to claim 8; further comprising:
- forming a slit on each guide ring so that a blade portion of a drill for boring a jaw bone can be inserted from a side face of the guide ring; and
- forming an opening portion having a width that is substantially the same as the slit or that expands outwardly and more widely than the slit at a position of the surgical guide body corresponding to the slit.

* * * * *